United States Patent
Hamilton, Jr.

(10) Patent No.: US 6,900,358 B2
(45) Date of Patent: May 31, 2005

(54) PROCESS FOR CATALYTIC HYDROXYLATION OF BENZENE

(75) Inventor: David Morris Hamilton, Jr., Sugar Land, TX (US)

(73) Assignee: Shell Oil Company, Houston, TX (US)

(*) Notice: Subject to any disclaimer, the term of this patent is extended or adjusted under 35 U.S.C. 154(b) by 122 days.

(21) Appl. No.: 09/841,654

(22) Filed: Apr. 24, 2001

(65) Prior Publication Data

US 2001/0044559 A1 Nov. 22, 2001

Related U.S. Application Data

(63) Continuation-in-part of application No. 09/559,925, filed on Apr. 27, 2000.

(51) Int. Cl.$^7$ ........................... C07C 37/00; C07C 37/60
(52) U.S. Cl. ..................... 568/802; 568/741; 568/771; 568/800
(58) Field of Search .................. 568/802, 800, 568/741, 771

(56) References Cited

U.S. PATENT DOCUMENTS

| | | | |
|---|---|---|---|
| 4,016,245 A | 4/1977 | Plank et al. | 423/328 |
| 4,251,499 A | 2/1981 | Nanne et al. | 423/329 |
| 4,439,409 A | 3/1984 | Puppe et al. | 423/328 |
| 4,683,217 A | 7/1987 | Lok et al. | 502/214 |
| 4,758,419 A | 7/1988 | Lok et al. | 423/306 |
| 4,795,623 A | 1/1989 | Evans | 423/328 |
| 4,826,667 A | 5/1989 | Zones et al. | 423/277 |
| 4,942,027 A | 7/1990 | Evans | 423/328 |
| 4,954,325 A | 9/1990 | Rubin et al. | 423/328 |
| 5,001,280 A | 3/1991 | Gubelmann et al. | 568/716 |
| 5,055,623 A | 10/1991 | Gubelmann et al. | 568/800 |
| 5,110,995 A | 5/1992 | Kharitonov et al. | 568/800 |
| 5,176,883 A | 1/1993 | Smith, Jr. et al. | 422/211 |
| 5,190,904 A | 3/1993 | Crossland et al. | 502/85 |
| 5,215,725 A | 6/1993 | Sy | 422/212 |
| 5,236,575 A | 8/1993 | Bennett et al. | 208/46 |
| 5,243,115 A | 9/1993 | Smith, Jr. et al. | 585/446 |
| 5,262,576 A | 11/1993 | Smith, Jr. | 585/447 |
| 5,321,181 A | 6/1994 | Smith, Jr. et al. | 585/467 |
| 5,324,702 A | 6/1994 | Yoo et al. | 502/204 |
| 5,345,006 A | 9/1994 | Smith, Jr. | 568/899 |
| 5,362,697 A | 11/1994 | Fung et al. | 502/71 |
| 5,446,223 A | 8/1995 | Smith, Jr. | 585/313 |
| 5,476,978 A | 12/1995 | Smith, Jr. et al. | 585/323 |
| 5,756,861 A | 5/1998 | Panov et al. | 568/800 |
| 5,762,777 A | 6/1998 | Yang et al. | 205/158 |
| 5,770,782 A | 6/1998 | Knifton et al. | 585/467 |
| 5,808,167 A | 9/1998 | McGhee | 568/716 |
| 5,827,491 A | 10/1998 | Emerson et al. | 423/328.2 |
| 5,874,646 A | 2/1999 | Ebner et al. | 568/771 |
| 5,912,391 A | 6/1999 | Barnhart et al. | 568/802 |
| 5,958,370 A | 9/1999 | Zones et al. | 423/706 |

FOREIGN PATENT DOCUMENTS

| | | | | |
|---|---|---|---|---|
| DE | 19634406 A1 | 3/1998 | | C07B/41/02 |
| EP | 0043562 A1 | 1/1982 | | C01B/25/36 |
| EP | 0158976 A2 | 10/1985 | | C01B/33/26 |
| GB | 2116974 A | 10/1983 | | C07C/37/60 |
| WO | WO 99/35087 | 7/1999 | | C01B/39/48 |

OTHER PUBLICATIONS

"Direct Hydroxylation of Benzene to Phenol by Nitrous Oxide," by A. K. Uriarte, M. A. Rodkin, M. J. Gross, A. S. Kharitonov, and G. I. Panov, 3rd World Congress on Oxidation Catalysis, 1997 Elsevier Science B.V., pp. 857–864.

Oxidative Hydroxylation Using Dinitrogen Monoxide: A Possible Route for Organic Synthesis Over Zeolites, by G. I. Panov, A. S. Kharitonov, and V. I. Sobolev, Applied Catalysis A: General, 98 (1993) pp. 1–20.

Chemical Communications, 1998, pp. 1841–1842.

"Isolated Redox Centers Within Microporous Environments 2. Vanadium–Containing Aluminophosphate Molecular Sieve Five," by C. Montes, M. E. Davis, B. Murray, and M. Narayana, *J. Phys. Chem.* 1990, 94, pp. 6431–6435.

"Isolated Redox Centers Within Microporous Environments 1. Cobalt–Containing Aluminophosphate Molecular Sieve Five," by C. Montes, M. E. Davis, B. Murray, and M. Narayana, *J. Phys. Chem.* 1990, 94, pp. 6425–6430.

*Primary Examiner*—Johann R. Richter
*Assistant Examiner*—Elvis O. Price

(57) ABSTRACT

A process for hydroxylating benzene under catalytic distillation conditions to produce hydroxylated products such as phenol is provided. The process provides for direct hydroxylation of liquid phase benzene with an oxidant and a zeolite catalyst under conditions effective to prevent coke formation on the catalyst.

88 Claims, 1 Drawing Sheet

PROCESS FOR CATALYTIC HYDROXYLATION OF BENZENE

This application is a continuation-in-part of application Ser. No. 09/559,925, filed Apr. 27, 2000, the entire disclosure of which is hereby incorporated by reference.

FIELD OF THE INVENTION

The present invention relates to a process for oxidizing benzene using an oxidant over an oxidizing catalyst under catalytic distillation conditions. More particularly, the present invention relates to hydroxylating benzene using an oxidizing gas over a molecular sieve catalyst under catalytic distillation conditions.

BACKGROUND OF THE INVENTION

Various methods are known to produce hydroxylated aromatic compounds. The majority of such processes require either the purchase or the formation of an aromatic compound bearing a substituent besides a hydroxyl group. That preexisting substituent then is converted to a hydroxyl group. Direct hydroxylation of aromatic compounds theoretically should be more economical.

Known methods for directly hydroxylating aromatics—particularly for directly converting benzene to phenol—are gas phase processes. In such processes, benzene vapor is partially oxidized at high temperature, typically by reaction with nitrous oxide over a catalyst bed.

Gas phase direct conversion processes are less than ideal for a number of reasons. The energy required to supply the initial heat to begin the reaction is costly. In addition, the reaction of benzene and nitrous oxide is highly exothermic. Expensive, complex system designs may be required to handle the excess heat.

The expense of such reactions is further increased by coke formation from the decomposition products formed at such high temperatures. The average productivity of a catalyst for gas phase oxidation of benzene is only about 4 mmol phenol/g catalyst/hour. The coked catalyst must be regenerated at frequent intervals.

Finally, the reported selectivity of nitrous oxide to phenol in these gas phase processes is low. While selectivities of benzene to phenol of 97–98 mol % are reported, the reported selectivity of nitrous oxide to phenol is only about 85 mol %.

A more economical and efficient process is needed for directly hydroxylating benzene.

SUMMARY OF THE INVENTION

The present invention provides a process comprising:

continuously contacting, in a distillation column reactor comprising a reaction zone and a distillation zone, benzene with a zeolite catalyst effective to hydroxylate benzene and an oxidant at a temperature in the range of from above 100° C. to 270° C. thereby producing a hydroxylated product, wherein at least a portion of said benzene being in a liquid phase;

continuously separating said hydroxylated product from the un-reacted benzene in the distillation zone under conditions effective to vaporize said un-reacted benzene and maintain said hydroxylated product in a liquid phase; and recovering the said hydroxylated product from the distillation column reactor.

DETAILED DESCRIPTION OF THE INVENTION

Figure 1:
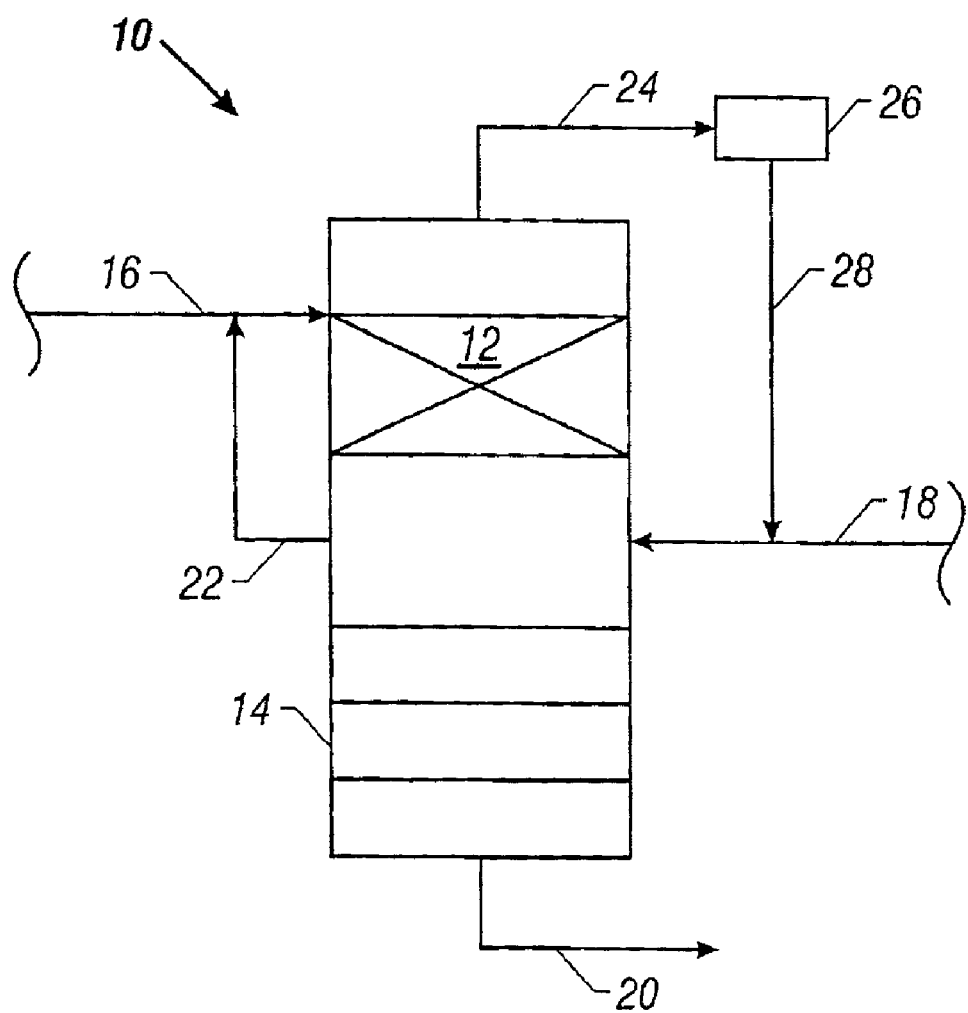
FIG. 1 is a schematic representation of one embodiment of the present invention using a distillation column reactor.

The present invention relates to a process for the direct hydroxylation of benzene under catalytic distillation conditions. A portion of the benzene is maintained in a liquid phase. Benzene is hydroxylated by an oxidant in the presence of an zeolitic oxidizing catalyst under conditions effective to hydroxylate benzene, and preferably maximizes the stability of the catalyst and the selectivity of the conversion of the oxidant to the hydroxylated product.

More particularly, the invention relates to a catalytic distillation process for the oxidative hydroxylation of benzene to form at least one hydroxylated derivative at a temperature and a pressure that maintains at least a portion of the benzene in the liquid phase and manages the heat generated by the exothermic hydroxylation reaction. Benzene can be hydroxylated to produce phenol and dihydroxylated products such as, for example, resorcinol, catechol and hydroquinone. Reflux of the un-reacted benzene renders the reaction substantially isothermic. Reduced operating temperatures and heat management maximize the catalyst life by reducing catalyst coking. The selectivity of the conversion of the oxidant to hydroxylated product also is increased to at least about 90 mol %, preferably to at least about 95 mol %, most preferably to at least about 99 mol %.

During catalytic distillation, the hydroxylation reaction occurs simultaneously with the distillation, the hydroxylated product being removed from the catalytic zone as it is formed. Removal of the hydroxylated product minimizes side reactions and decomposition of the hydroxylated product. The distillation zone of the reactor is maintained at a temperature and a pressure sufficient to maintain any un-reacted benzene that travels from the catalytic zone to the distillation zone in the vapor phase, preferably at or above the boiling point of benzene at a given pressure. The catalytic zone is maintained at a temperature that is below the boiling point of the hydroxylated product, e.g., phenol. The un-reacted benzene eventually reaches a point in the reactor where it boils, and as a result, the temperature of the reactor is controlled by the boiling point of the aromatic compound at the system pressure. The exothermic heat of the hydroxylation reaction will vaporize a portion of the un-reacted benzene but will not increase the temperature in the reactor. The hydroxylation reaction has an increased driving force because the hydroxylated product, e.g., phenol, is removed and cannot contribute to a reverse reaction.

In a preferred process, benzene is hydroxylated using catalytic distillation to form a hydroxylated product having a higher boiling point than benzene. The hydroxylation reaction is catalyzed by zeolite catalyst in the presence of an oxidant in a catalytic distillation reactor (distillation column reactor) at conditions that also allow for fractional distillation. The hydroxylation preferably is carried out using the zeolite catalyst, under conditions that maintain at least part of the benzene in a liquid phase. The catalytic distillation reactor preferably provides both catalytic zones and distillation zones. The "catalytic zone" is defined as the portion of the reactor containing the catalyst where the oxidant and benzene react to form hydroxylated product. The "distillation zone," also called the "fractionation zone," is defined as the portion of the reactor adapted to separate the hydroxylated product from the un-reacted benzene. The distillation zone is a conventional fractionation column design, preferably integral with and downstream of the reaction zone.

The hydroxylated product has a higher boiling point than the oxidant and the benzene, and is separated from un-reacted benzene in the distillation zone of the reactor. The temperature along the reactor will vary depending upon the reactants and the products. The highest temperature will be in the bottom of the reactor, in the distillation zone, and the temperature along the column will be the boiling point of the composition at that point in the column under a given pressure. The reactor preferably is operated at a temperature and a pressure effective to vaporize benzene as it approaches the distillation zone of the reactor while maintaining the hydroxlyated product, e.g., phenol, in the liquid phase. The oxidant preferably remains in a gaseous state and un-reacted oxidant is withdrawn as overhead. The hydroxylated product, e.g., phenol, is withdrawn from the distillation zone and any un-reacted benzene may be allowed to reflux or it may be withdrawn from the distillation zone and added to the original benzene feed as makeup.

In the catalytic distillation reactor, there exists both a liquid phase, or internal reflux, and a vapor phase. The liquid phase is more dense than a gas phase and allows for a more dense concentration of molecules for reaction over the catalyst. The fractionation or distillation separates hydroxylated product from un-reacted materials, providing the benefits of a combined liquid phase and vapor phase system while avoiding continual contact between the catalyst, the reactants, and the products.

A number of possible catalytic distillation reactor configurations are useful with the present invention, including but not limited to an upflow reactor, a downflow reactor, and a horizontal flow reactor. The reactor contains a reaction or catalytic zone sized to accommodate a fixed catalyst and a distillation zone designed to separate the hydroxylated product from un-reacted materials. The distillation zone is integral with the reaction or catalytic zones Examples of suitable catalytic distillation reactors are found in U.S. Pat. Nos. 5,476,978; 5,262,576; 5,176,883; 5,243,115; 5,321,181; 5,345,006; 5,215,725; 5,770,782; 5,446,223; and 5,190,904, which are hereby incorporated by reference.

Specific catalytic distillation column design and process conditions will vary depending upon the reactants used. The design temperature and pressure can be adjusted based on the properties of the reactants including benzene and the oxidant, to effectively hydroxylate benzene and to separate the hydroxylated product from the reactants based on their respective boiling points at a given pressure.

In a preferred embodiment, the catalytic zone and the distillation zone are in a single column. The catalytic zone contains an amount of catalyst and the distillation zone contains a number of conventional separation trays. Benzene preferably is delivered to the column above the catalyst and the oxidant is fed to the column below the catalyst. Any un-reacted benzene is either withdrawn from the column once it leaves the catalytic zone, preferably as a vapor, and supplied as makeup or allowed to reflux. The overhead is withdrawn from the column above the catalytic zone and typically will contain a mixture consisting mostly of oxidant and a small amount of benzene. The oxidant preferably is separated from benzene by conventional means and recycled as makeup.

Suitable zeolite catalysts are those that will catalyze the hydroxylation of benzene in the presence of an oxidant. Preferred zeolite catalysts contain one or more modified zeolites preferably in the acidic form. These zeolites should contain pore dimensions large enough to admit the entry of the reactants. The preferred zeolites include, for example, zeolites of the structural types MFI (e.g., ZSM-5), MEL (e.g., ZSM-11), FER (e.g., ferrierite and ZSM-35), FAU (e.g., zeolite Y), BEA (e.g., beta), MFS (e.g., ZSM-57), NES (e.g. NU-87), MOR (e.g. mordenite), MTT (e.g., ZSM-23), MWW (e.g., MCM-22 and SSZ-25), EUO (e.g. EU-1, ZSM-50, and TPZ-3), OFF (e.g., offretite), MTW (e.g., ZSM-12) and zeolites ITQ-1, ITQ-2, MCM-56, MCM-49, ZSM-48, SSZ-35, and zeolites of the mixed crystalline phases such as, for example, zeolite PSH-3. The structural types and references to the synthesis of the various zeolites can be found in the "Atlas of Zeolite Structure Types" (published on behalf of the Structure Commission of the International Zeolite Association), by W. M. Meier, D. H. Olson and Ch. Baerlocher, published by Butterworth-Heinemann, fourth revised edition, 1996. Structural types and references to the zeolites mentioned above are available on the World Wide Web at www.iza-structure.org Such zeolites are commercially available from Zeolyst International, Inc. and ExxonMobil Corporation. More preferably, the zeolite is a crystalline alumino-silicate that can contain trace amounts of boron from raw materials without on purpose adding boron sources to enrich boron content.

The zeolite catalyst preferably comprises at least one metal selected from the group consisting of ruthenium, rhodium, iron, magnesium, cobalt, copper, titanium, vanadium, manganese, niobium, and iridium, preferably from about 0.01 wt. % to about 5 wt. %, most preferably from about 0.1 wt. % to about 1.5 wt. %. The metal can be incorporated into the catalyst by any means known to those skilled in the art for incorporating metals into zeolites such as, by ion exchange, impregnation, co-mulling, physical admixing or during synthesis of the catalyst. In a preferred embodiment, the zeolite catalyst contains an amount of iron, preferably up to about 5 wt. %, more preferably from about 0.01 wt. % to about 1.5 wt. %. Additional examples of suitable zeolite catalysts can be found in U.S. Pat. Nos. 5,762,777; 5,808,167; 5,110,995; 5,874,646; 4,826,667; 4,439,409; 4,954,325; 5,236,575; 5,362,697; 5,827,491; 5,958,370; 4,016,245; 4,251,499; 4,795,623; 4,942,027 and WO99/35087, which are hereby incorporated by reference.

Any suitable oxidant may be used. Examples of oxidant (oxidizing gases) include but are not necessarily limited to, nitrous oxide, oxygen, air, and mixtures thereof. A preferred oxidant for use with zeolite catalysts is nitrous oxide. Regardless of the oxidant used, the molar ratio of oxidant to aromatic compound is from about 1:1000 to about 100:1, preferably from about 1:1000 to about 10:1, most preferably from about 1:100 to about 1:1. In practice, the oxidant to organic compound ratio is the stoichiometric ratio that will yield the desired product and allow safe operation.

In a preferred embodiment, catalytic distillation is carried out in a distillation column reactor at a temperature and a pressure effective to hydroxylate the benzene while fractionating or removing the hydroxylated product, e.g., phenol, from the oxidant and un-reacted benzene. The temperature in the distillation zone of the reactor is higher than the temperature in the catalytic zone of the reactor. The temperature within the reactor is such that the lower boiling components are vaporized and migrate toward the upper portion of the reactor while the higher boiling components migrate toward the lower portion of the reactor. For benzene, the temperature that the reaction is carried out in the distillation column reactor is within the range of from above 100° C., preferably from about 185° C., more preferably from about 200° C., to about 270° C., preferably to about 250° C. The temperature in the lower portion of the column preferably is higher than the boiling point of benzene but lower than the boiling point of the hydroxylated product, e.g., phenol, to achieve an effective separation of the hydroxylated product, e.g., phenol, from the benzene.

The pressure in the column is from about 0.2 atm to about 50 atm, preferably from about 0.5 atm to about 30 atm. Partial pressure of the benzene feed in the column is in the range of from about 0.1 atm, preferably from 10 atm, to about 45 atm, preferably to about 30 atm. Inert (not reactive to the reactants) gases, such as for example, nitrogen and argon can be used to dilute the reactants to achieve a lower partial pressure of the reactants.

The benzene may be added at any point in the reactor, for example it may be added above or to the fixed bed catalyst or to the reflux as makeup. At least a portion of the benzene, preferably from about 10% to about 100%, is fed to the reactor in a liquid state. The oxidant preferably is a gas, and is fed to the reactor at a point below the catalyst bed allowing the oxidant to flow upward into the catalyst bed where the oxidant contacts and reacts with the benzene. Once in the reactor, the benzene contacts the catalyst and the oxidant, and the benzene is hydroxylated to form phenol. Phenol has a higher boiling point (182° C.) than benzene (80° C.), which allows for easy separation by fractional distillation.

The overhead taken from the distillation column preferably is partially condensed to separate the un-reacted benzene from the un-reacted oxidant. The partially condensed overheads are passed to an accumulator where benzene is collected and the gaseous oxidant is taken off. The benzene and the oxidant can be fed back to the distillation column. Preferably, heat generated by the hydroxylation reaction is removed from the reactor by the reflux of the un-reacted benzene, allowing for isothermal operation of the system. Regulating the heat in the reactor also extends the catalyst life.

The zeolite catalyst is believed to catalyze the following reaction, when the reactants are benzene and nitrous oxide and the hydroxylated product is phenol:

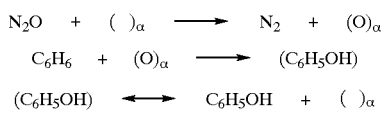

where the formation of the alpha oxygen $(O)_\alpha$ is critical. The formation of $(O)_\alpha$ is dependent upon the metal content of the zeolite catalyst. The $(O)_\alpha$ will form at low temperatures provided there is sufficient metal (e.g.,iron) present in the zeolite. Once the $(O)_\alpha$ has formed, desorption of $(O)_\alpha$ as $O_2$ does not occur at temperatures below 300° C. to 330° C., which means that $(O)_\alpha$ can be isolated on the catalyst at moderate temperatures. It is believed that the $(O)_\alpha$ oxygen from the $N_2O$ will remain on the catalyst until it is reacted with the benzene, thus increasing the amount of $(O)_\alpha$ used to form phenol. It has been shown that benzene will react with $(O)_\alpha$ at ambient temperatures (e.g. 50° C.) to form phenol at high yields. However, the phenol formed is bound to the catalyst. It is believed that oxidative hydroxylation under catalytic distillation conditions will prevent the hydroxylated product from binding to the catalyst.

FIG. 1 illustrates one embodiment of the present invention for the production of phenol. A distillation column reactor 10 has a middle portion that contains a catalyst 12 and a lower portion of the reactor contains a conventional distillation column 14 with a sufficient number of trays to allow for the separation of the phenol product from any un-reacted benzene. The benzene is fed to the reactor through line 16 above the catalyst 12 and the oxidant gas is fed to reactor 10 through line 18 below the catalyst 12. The reaction is exothermic and is initiated by contacting the oxidant and the benzene in the presence of the catalyst. Phenol is the principal reaction product. Phenol has a higher boiling point than the benzene and the oxidant and is recovered from the column via line 20. The temperature in the reactor below the catalyst bed is higher than the boiling point of benzene and lower than the boiling point of phenol to facilitate the separation of the benzene from the phenol. Un-reacted benzene can be withdrawn from the reactor 10 via line 22 and added as makeup to the benzene fed through line 16 into the reactor 10. Alternatively, the un-reacted benzene is allowed to reflux. The oxidant is withdrawn as overhead through line 24 and passed to a condenser 26 to separate any entrained benzene from the oxidant. The recovered oxidant may then be added as makeup via line 28 to the fresh oxidant feed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

I claim:

1. A process comprising:
    providing a distillation column reactor comprising oxidation catalyst between a distillation zone and a reaction zone;
    feeding liquid benzene to the reaction zone;
    feeding oxidant gas to the distillation zone;
    contacting benzene and oxidant gas with the oxidation catalyst under oxidation conditions effective to catalytically hydroxylate at least a portion of the benzene to produce hydroxylated product.

2. The method of claim 1 further comprising separating hydroxylated product from the distillation zone.

3. The method of claim 1 wherein the oxidation catalyst comprises zeolite catalyst.

4. The method of claim 2 wherein the oxidation catalyst comprises zeolite catalyst.

5. The method of claim 1 wherein the oxidation conditions comprise a temperature of from above 100° C. to 270° C.

6. The method of claim 2 wherein the oxidation conditions comprise a temperature of from above 100° C. to 270° C.

7. The method of claim 4 wherein the oxidation conditions comprise a temperature of from above 100° C. to 270° C.

8. The method of claim 2 wherein the separating hydroxylated product from the distillation zone comprises
    maintaining un-reacted benzene in the distillation zone under conditions effective to vaporize the un-reacted benzene and maintain hydroxylated product in a liquid phase; and
    recovering at least a portion of the liquid phase from the distillation zone.

9. The method of claim 4 wherein the separating hydroxylated product in the distillation zone comprises
    maintaining un-reacted benzene in the distillation zone under conditions effective to vaporize the un-reacted benzene and maintain hydroxylated product in a liquid phase; and
    recovering at least a portion of the liquid phase from the distillation zone.

10. The method of claim 7 wherein the separating hydroxylated product from the distillation zone comprises maintaining un-reacted benzene in the distillation zone under conditions effective to vaporize the un-reacted benzene and maintain hydroxylated product in a liquid phase; and recovering at least a portion of the liquid phase from the distillation zone.

11. The process of claim 8 wherein said recovering at least a portion of the liquid phase from the distillation zone comprises substantially continuous fractional distillation.

12. The process of claim 9 wherein said recovering at least a portion of the liquid phase from the distillation zone comprises substantially continuous fractional distillation.

13. The process of claim 1 wherein the oxidant gas is selected from the group consisting of nitrous oxide, oxygen, air, and mixtures thereof.

14. The process of claim 10 wherein the oxidant is selected from the group consisting of nitrous oxide, oxygen, air and mixtures thereof.

15. The process of claim 1 wherein the oxidant gas comprises nitrous oxide.

16. The process of claim 4 wherein the oxidant gas comprises nitrous oxide.

17. The process of claim 7 wherein the oxidant gas comprises nitrous oxide.

18. The process of claim 10 wherein the oxidant gas comprises nitrous oxide.

19. The process of claim 1 wherein the oxidation conditions comprise a temperature of from about 185° C. to about 270° C.

20. The process of claim 4 wherein the conditions comprise a temperature of from about 185° C. to about 270° C.

21. The process of claim 10 wherein the conditions comprise a temperature of from about 185° C. to about 270° C.

22. The process of claim 14 wherein the conditions comprise a temperature of from about 185° C. to about 70° C.

23. The process of claim 1 wherein selectivity for conversion of the oxidant gas to hydroxylated product is at least 90 mol %.

24. The process of claim 10 wherein selectivity for conversion of the oxidant gas to hydroxylated product is at least 90 mol %.

25. The process of claim 10 wherein selectivity for conversion of the oxidant to hydroxylated product is at least 95 mol %.

26. The process of claim 1 wherein the oxidation catalyst comprises zeolite catalyst comprising at least one metal selected from the group consisting of ruthenium, rhodium, iridium, iron, magnesium, cobalt, copper, titanium, vanadium, manganese, niobium, and mixtures thereof.

27. The process of claim 7 wherein the oxidation catalyst comprises zeolite catalyst comprising at least one metal selected from the group consisting of ruthenium, rhodium, iridium, iron, magnesium, cobalt, copper, titanium, vanadium, manganese, niobium, and mixtures thereof.

28. The process of claim 10 wherein the oxidation catalyst comprises zeolite catalyst comprising at least one metal selected from the group consisting of ruthenium, rhodium, iridium, iron, magnesium, cobalt, copper, titanium, vanadium, manganese, niobium, and mixtures thereof.

29. The process of claim 14 wherein the oxidation catalyst comprises zeolite catalyst comprising at least one metal selected from the group consisting of ruthenium, rhodium, iridium, iron, magnesium, cobalt, copper, titanium, vanadium, manganese, niobium, and mixtures thereof.

30. The process of claim 26 wherein the zeolite catalyst comprises the metal in an amount of from about 0.01 wt % to about 5 wt %.

31. The process of claim 27 wherein the zeolite catalyst comprises metal in an amount of from about 0.01 wt % to about 5 wt %.

32. The process of claim 28 wherein the zeolite catalyst comprises metal in amount from about 0.01 wt % to about 5 wt %.

33. The process of claim 29 wherein the zeolite catalyst comprises metal in amount from about 0.01 wt % iron to about 5 wt % iron.

34. The process of claim 1 wherein the oxidation conditions comprise a temperature of from about 185° C. to about 270° C.

35. The process of claim 33 wherein the oxidation conditions comprise a temperature of from about 185° C. to about 270° C.

36. The process of claim 34 wherein the oxidation conditions comprise a benzene partial pressure in the range of from about 0.1 atm to about 45 atm.

37. The process of claim 35 wherein the oxidation conditions comprise a benzene partial pressure in the range of from about 0.1 atm to about 45 atm.

38. The process of claim 1 further comprising withdrawing un-reacted benzene and oxidant gas as overhead.

39. The process of claim 1 wherein the temperature of the distillation zone is higher than the boiling point of benzene and lower than the boiling point of phenol.

40. The process of claim 14 wherein the temperature of the distillation zone is higher than the boiling point of benzene and lower than the boiling point of phenol.

41. The process of claim 36 wherein the temperature of the distillation zone is higher than the boiling point of benzene and lower than the boiling point of phenol.

42. The process of claim 37 wherein the temperature of the distillation zone is higher than the boiling point of benzene and lower than the boiling point of phenol.

43. A process comprising
providing a distillation column reactor comprising oxidation catalyst between a distillation zone and a reaction zone;
feeding liquid benzene to the reaction zone;
feeding oxidant gas to the distillation zone;
contacting the benzene and the oxidant gas with the oxidation catalyst under oxidation conditions effective to catalytically hydroxylate at least a portion of the benzene to produce hydroxylated product, the oxidation conditions comprising a temperature of from above 100° C. to 270° C. and a benzene partial pressure in the range of from about 0.1 atm to about 45 atm;
separating hydroxylated product from the distillation zone.

44. The method of claim 43 wherein separating hydroxylated product from the distillation zone comprises
maintaining un-reacted benzene in the distillation zone under conditions effective to vaporize the un-reacted benzene and maintain hydroxylated product in a liquid phase; and
recovering at least a portion of the liquid phase from the distillation zone.

45. The process of claim 43 wherein the separating hydroxylated product from the distillation zone comprises substantially continuous fractional distillation.

46. The process of claim 44 wherein the separating hydroxylated product from the distillation column reactor comprises substantially continuous fractional distillation.

47. The process of claim 43 wherein the oxidant gas is selected from the group consisting of nitrous oxide, oxygen, air, and mixtures thereof.

48. The process of claim 44 wherein the oxidant gas is selected from the group consisting of nitrous oxide, oxygen, air, and mixtures thereof.

49. The process of claim 46 wherein the oxidant gas is selected from the group consisting of nitrous oxide, oxygen, air, and mixtures thereof.

50. The process of claim 43 wherein the oxidant gas comprises nitrous oxide.

51. The process of claim 44 wherein the oxidant gas comprises nitrous oxide.

52. The process of claim 46 wherein the oxidant gas comprises nitrous oxide.

53. The process of claim 43 wherein the oxidation conditions comprise a temperature of from about 185° C. to about 270°.

54. The process of claim 50 wherein the conditions comprise a temperature of from about 185° C. to about 270°.

55. The process of claim 51 wherein the conditions comprise a temperature of from about 185° C. to about 270°.

56. The process of claim 52 wherein the conditions comprise a temperature of from about 185° C. to about 270°.

57. The process of claim 43 wherein selectivity for conversion of the oxidant gas to hydroxylated product is at least 90 mol %.

58. The process of claim 43 wherein selectivity for conversion of the oxidant gas to hydroxylated product is at least 95 mol %.

59. The process of claim 43 wherein the oxidation catalyst comprises a zeolite catalyst comprising at least one metal selected from the group consisting of ruthenium, rhodium, iridium, iron, magnesium, cobalt, copper, titanium, vanadium, manganese, niobium, and mixtures thereof.

60. The process of claim 51 wherein the oxidation catalyst comprises a zeolite catalyst comprising at least one metal selected from the group consisting of ruthenium, rhodium, iridium, iron, magnesium, cobalt, copper, titanium, vanadium, manganese, niobium, and mixtures thereof.

61. The process of claim 52 wherein the oxidation catalyst comprises a zeolite catalyst comprising at least one metal selected from the group consisting of ruthenium, rhodium, iridium, iron, magnesium, cobalt, copper, titanium, vanadium, manganese, niobium, and mixtures thereof.

62. The process of claim 56 wherein the oxidation catalyst comprises a zeolite catalyst comprising at least one metal selected from the group consisting of ruthenium, rhodium, iridium, iron, magnesium, cobalt, copper, titanium, vanadium, manganese, niobium, and mixtures thereof.

63. The process of claim 59 wherein the zeolite catalyst comprises the metal in an amount of about 0.01 wt % to about 5 wt %.

64. The process of claim 60 wherein the zeolite catalyst comprises metal in an amount of from about 0.01 wt % to about 5 wt %.

65. The process of claim 61 wherein the zeolite catalyst comprises metal in an amount from about 0.01 wt % to about 5 wt %.

66. The process of claim 62 wherein the zeolite catalyst comprises metal in an amount from about 0.01 wt % iron to about 5 wt % iron.

67. The process of claim 43 wherein the oxidation conditions comprise a temperature of from about 185° C. to about 270°.

68. The process of claim 66 wherein the oxidation conditions comprise a temperature of from about 185° C. to about 270°.

69. The process of claim 43 further comprising withdrawing un-reacted benzene and oxidant gas as overhead.

70. The process of claim 43 wherein the temperature of the distillation zone is higher than the boiling point of benzene and lower than the boiling point of phenol.

71. The process of claim 43 wherein selectivity for conversion of nitrous oxide to phenol is at least about 90 mol %.

72. The process of claim 43 wherein the zeolite catalyst comprises from about 0.01 wt % to about 5 wt % of at least one metal selected from the group consisting of ruthenium, rhodium, iridium, titanium, magnesium, cobalt, copper, vanadium, manganese, niobium, and iron.

73. The process of claim 56 wherein the zeolite catalyst comprises from about 0.01 wt % to about 5 wt % of at least one metal selected from the group consisting of ruthenium, rhodium, iridium, titanium, magnesium, cobalt, copper, vanadium, manganese, niobium, and iron.

74. A process comprising
providing a distillation column reactor comprising oxidation catalyst located between a distillation zone and a reaction zone, the oxidation catalyst comprising zeolite catalyst comprising from about 0.01 wt % to about 5 wt % of at least one metal selected from the group consisting of ruthenium, rhodium, iridium, titanium, magnesium, cobalt, copper, vanadium, manganese, niobium, and iron;
feeding liquid benzene to the reaction zone;
feeding nitrous oxide to the distillation zone;
contacting the benzene and the oxidant gas with the oxidation catalyst under oxidation conditions effective to catalytically hydroxylate at least a portion of the benzene to produce hydroxylated product comprising phenol, the oxidation conditions comprising a temperature of from above 100° C. to 270° C. and a benzene partial pressure in the range of from about 0.1 atm to about 45 atm;
separating liquid phenol from the distillation zone.

75. The process of claim 74 wherein the temperature of the distillation zone is higher than the boiling point of benzene and lower than the boiling point of phenol.

76. The process of claim 74 wherein the at least one metal comprises iron.

77. The process of claim 76 wherein the zeolite catalyst comprises from about 0.1 wt. % iron to about 1.0 wt. % iron.

78. The process of claim 77 wherein the zeolite is an alumino-silicate produced without addition of boron.

79. The process of claim 74 wherein the separating liquid phenol from the distillation zone comprises substantially continuous fractional distillation.

80. The process of claim 78 wherein the separating liquid phenol from the distillation zone comprises substantially continuous fractional distillation.

81. The process of claim 74 wherein the oxidation conditions comprise temperature of from about 185° C. to about 270°.

82. The process of claim 80 wherein the conditions comprise a temperature of from about 185° C. to about 270°.

83. The process of claim 74 wherein selectivity for conversion of the oxidant gas to hydroxylated product is at least 90 mol %.

84. The process of claim 74 wherein selectivity for conversion of the oxidant gas to hydroxylated product is at least 95 mol %.

85. The process of claim 74 wherein the zeolite catalyst comprises at least one zeolite having a structural type selected from the group consisting of MFI, MEL, FER, FAU, BEA, MFS, NES, MOR, MTT, MWW, EUO, OFF, MTW and zeolites ITQ-1, ITQ-2, MCM-56, MCM-49, ZSM-48, SSZ-35, SSZ-39, and PHS-3 and mixtures thereof.

86. The process of claim 78 wherein the zeolite catalyst comprises at least one zeolite having a structural type selected from the group consisting of MFI, MEL, FER, FAU, BEA, MFS, NES, MOR, MTT, MWW, EUO, OFF, MTW and zeolites ITQ-1, ITQ-2, MCM-56, MCM-49, ZSM-48, SSZ-35, SSZ-39, and PSH-3 and mixtures thereof.

87. The process of claim 80 wherein the zeolite catalyst comprises at least one zeolite having a structural type selected from the group consisting of MFI, MEL, FER, FAU, BEA, MFS, NES, MOR, MTT, MWW, EUO, OFF, MTW and zeolites ITQ-1, ITQ-2, MCM-56, MCM-49, ZSM-48, SSZ-35, SSZ-39, and PSH-3 and mixtures thereof.

88. The process of claim 82 wherein the zeolite catalyst comprises at least one zeolite having a structural type selected from the group consisting of MFI, MEL, FER, FAU, BEA, MFS, NES, MOR, MTT, MWW, EUO, OFF, MTW and zeolites ITQ-1, ITQ-2, MCM-56, MCM-49, ZSM-48, SSZ-35, SSZ-39, and PSH-3 and mixtures thereof.

* * * * *